(12) United States Patent
Merza et al.

(10) Patent No.: US 12,070,230 B2
(45) Date of Patent: *Aug. 27, 2024

(54) ELECTROMECHANICAL SLIDER VALVE SUCTION CONTROLLER

(71) Applicant: Gyrus ACMI, Inc., Southborough, MA (US)

(72) Inventors: Saeed A Merza, Cordova, TN (US); Joey Magno, Cordova, TN (US); David C. Church, Millington, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 1292 days.

This patent is subject to a terminal disclaimer.

(21) Appl. No.: 16/713,994

(22) Filed: Dec. 13, 2019

(65) Prior Publication Data

US 2020/0113580 A1 Apr. 16, 2020

Related U.S. Application Data

(63) Continuation of application No. 15/278,243, filed on Sep. 28, 2016, now Pat. No. 10,537,336.

(51) Int. Cl.
*A61B 17/14* (2006.01)
*A61M 39/28* (2006.01)

(52) U.S. Cl.
CPC ........... *A61B 17/142* (2016.11); *A61M 39/28* (2013.01); *A61B 2217/005* (2013.01)

(58) Field of Classification Search
CPC . A61B 17/142; A61B 2217/005; A61M 39/28
USPC ....................................................... 604/319
See application file for complete search history.

(56) References Cited

U.S. PATENT DOCUMENTS

| | | | | |
|---|---|---|---|---|
| 4,735,610 A | * | 4/1988 | Akkas | A61M 1/772 604/319 |
| 5,217,478 A | * | 6/1993 | Rexroth | A61B 17/32002 606/180 |
| 5,318,576 A | * | 6/1994 | Plassche, Jr. | A61B 17/320725 606/159 |
| 5,922,003 A | | 7/1999 | Anctil et al. | |
| 6,312,441 B1 | | 11/2001 | Deng | |

(Continued)

FOREIGN PATENT DOCUMENTS

| | | |
|---|---|---|
| JP | S5675131 A | 6/1981 |
| JP | 2007160109 A | 6/2007 |

(Continued)

OTHER PUBLICATIONS

"U.S. Appl. No. 15/278,243, Final Office Action mailed Feb. 5, 2019", 10 pgs.

(Continued)

*Primary Examiner* — Andrew J Mensh
(74) *Attorney, Agent, or Firm* — Schwegman Lundberg & Woessner, P.A.

(57) ABSTRACT

Disclosed herein is a fluid management assembly. The fluid management assembly includes a handpiece, a slider based fluid control mechanism, and a fluid occluding member. The slider based fluid control mechanism housed in the handpiece. The fluid occluding member is configured to be in communication with the fluid control mechanism. The fluid occluding member being separate from the handpiece.

17 Claims, 6 Drawing Sheets

(56) References Cited

U.S. PATENT DOCUMENTS

| | | | |
|---|---|---|---|
| 6,689,146 B1 * | 2/2004 | Himes | A61B 17/32002 606/167 |
| 7,455,679 B2 | 11/2008 | Adams et al. | |
| 7,947,039 B2 * | 5/2011 | Sartor | A61B 18/1482 606/49 |
| 8,460,297 B2 | 6/2013 | Watlington et al. | |
| 10,537,336 B2 | 1/2020 | Merza et al. | |
| 2002/0035364 A1 * | 3/2002 | Schoenman | H01H 9/06 606/45 |
| 2010/0249703 A1 | 9/2010 | Cliff | |
| 2013/0149660 A1 | 6/2013 | Pruckner et al. | |
| 2018/0049920 A1 | 2/2018 | Charles | |
| 2018/0085131 A1 | 3/2018 | Merza et al. | |

FOREIGN PATENT DOCUMENTS

| | | |
|---|---|---|
| JP | 2008035922 A | 2/2008 |
| JP | 2018051287 A | 4/2018 |
| JP | 6887859 B2 | 5/2021 |
| WO | WO-02/24084 A1 | 3/2002 |
| WO | WO-2013/181555 A1 | 12/2013 |

OTHER PUBLICATIONS

"U.S. Appl. No. 15/278,243, Non Final Office Action mailed Sep. 24, 2018", 9 pgs.

"U.S. Appl. No. 15/278,243, Notice of Allowance mailed Sep. 25, 2019", 5 pgs.

"U.S. Appl. No. 15/278,243, Response filed May 6, 2019 to Final Office Action mailed Feb. 5, 2019", 12 pgs.

"U.S. Appl. No. 15/278,243, Response filed Dec. 26, 2018 to Non Final Office Action mailed Sep. 24, 2018", 8 pgs.

"Japanese Application Serial No. 2017-81754, Office Action mailed Nov. 24, 2020", with English Translation, 9 pgs.

"Japanese Application Serial No. 2017-81754, Response filed Feb. 24, 2021 to Office Action mailed Nov. 24, 2020", w/English Claims, 6 pgs.

"The Formula For Success—CORE Arthroscopic Shaver System", Stryker Endoscopy, 2007, 6 pgs.

Energy THUNDERBEAT Generators (ESG 400 & USG 400), (2016, Sep. 27), Retrieved Sep. 27, 2016, from http://medical.olympusamerica.com/products/thunderbeat-generatiors-esg-400-usg-400, 2 pgs.

Miniature Proportional Pinch Valve Series, (Sep. 27, 2016), Retrieved Sep. 27, 2016, from http://www.resolutionair.com/wp-content/uploads/2015/06/MPPV_tds.pdf, 2 pgs.

"Crossfire™ Console REF 0475000000" Stryker User Guide, 2009, 48 pgs.

* cited by examiner

UNRESTRICTED FLOW    RESTRICTED FLOW

ELECTROMECHANICAL SLIDER VALVE SUCTION CONTROLLER

CROSS REFERENCE TO RELATED APPLICATION

This is a continuation application of copending application Ser. No. 15/278,243 filed Sep. 28, 2016 which is hereby incorporated by reference in its entirety.

BACKGROUND

Field of the Invention

The invention relates to a fluid management assembly, and more specifically relates to an electromechanical slider valve suction controller.

Brief Description of Prior Developments

Many of the conventional medical orthopedic shavers have a suction path to aspirate fluid and other remnants from a patient's joint such as knee, elbow, shoulder, ankle and wrist to waste. The suction pathway generally requires a valve to control the amplitude of suction during surgical procedures. Many of the current orthopedics medical shaver handpiece devices have a mechanical valve which enables the user to control the suction through the suction cannula.

FIG. 1 illustrates a conventional orthopedics handpiece shaver device 10 having a housing 12 which surrounds a motor 14, a gearbox 16, and a coupler 18. The device 10 is configured such that a blade (or any other suitable attachment) is removably attachable to a front end of the device 10. The device 10 further comprises a suction control valve 20 and a suction cannula 22. A back end of the device 10 is configured to receive a cable 24 for connection to the motor 14. Additionally, buttons 26 are provided for user control of the device 10.

As shown in FIG. 1, the mechanical valve 20 is integrated within the cannula of a handpiece shaver suction path. This generally results in various limitations and disadvantages.

SUMMARY

In accordance with one aspect of the invention, a fluid management assembly is disclosed. The fluid management assembly includes a handpiece, a slider based fluid control mechanism, and a fluid occluding member. The slider based fluid control mechanism housed in the handpiece. The fluid occluding member is configured to be in communication with the fluid control mechanism. The fluid occluding member being separate from the handpiece.

In accordance with another aspect of the invention, a method is disclosed. A handpiece is provided. A slider based fluid control mechanism is connected to the handpiece. A fluid occluding member configured to be in communication with the fluid control mechanism is provided. The fluid occluding member is separate from the handpiece.

BRIEF DESCRIPTION OF THE DRAWINGS

The foregoing aspects and other features of the invention are explained in the following description, taken in connection with the accompanying drawings, wherein.

DETAILED DESCRIPTION

Figure 2:
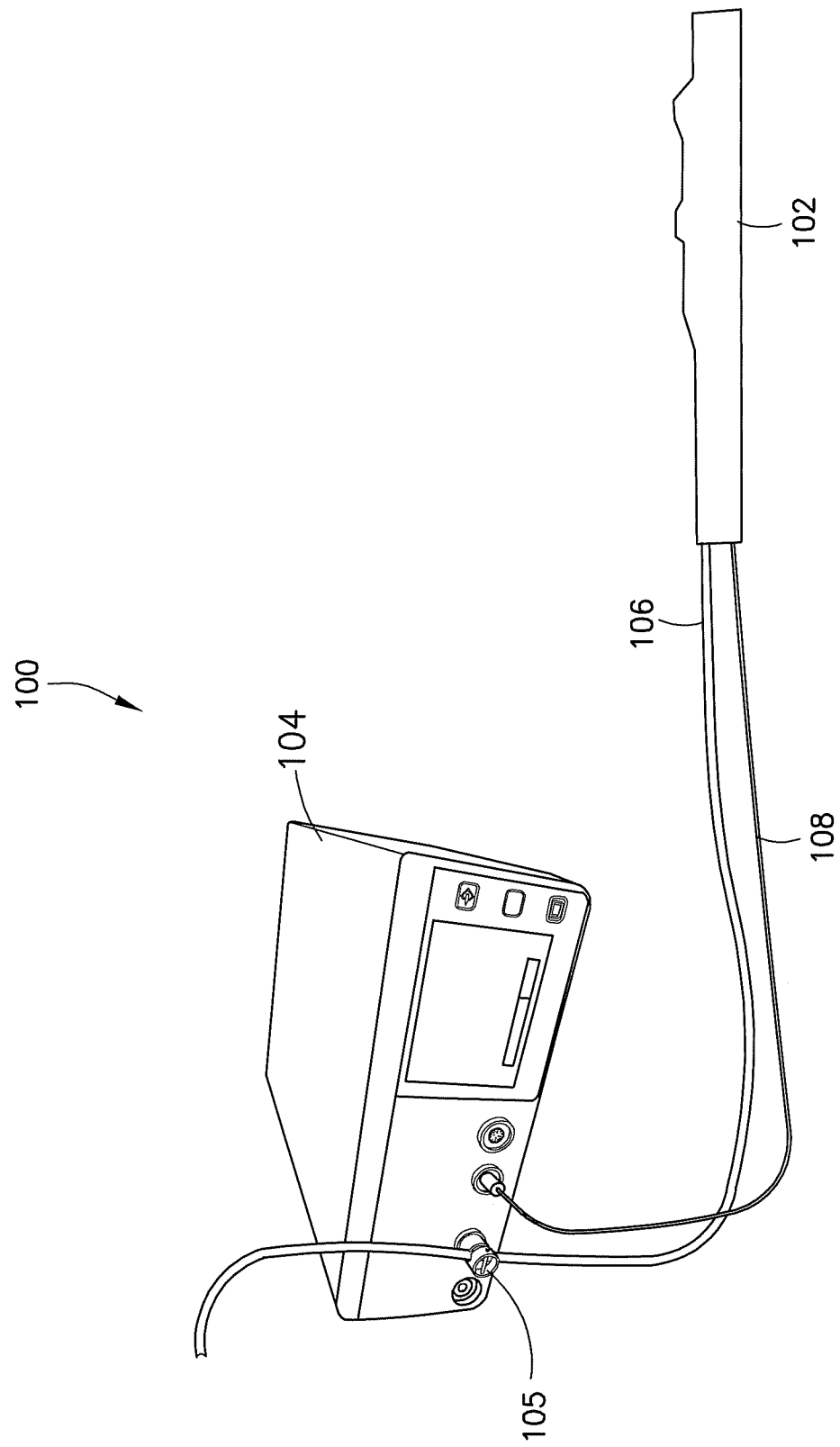
FIG. 2 is a perspective view of a fluid management system incorporating features of the invention.

Referring to FIG. 2, there is shown a perspective view of a fluid management system 100 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The fluid management system 100 includes a handpiece 102 and console 104. A shaver tubeset 106 is connected between the console 104 and the handpiece 102. The tubeset 106 is connected to the console 104 through a valve 105. Additionally, a power cable 108 is connected between the console 104 and the handpiece 102.

According to various exemplary embodiments, the console 104 may be a shaver console available from Stryker Corporation. However in alternate embodiments, any suitable type of shaver console, or variations thereof, may be provided.

Figure 3:
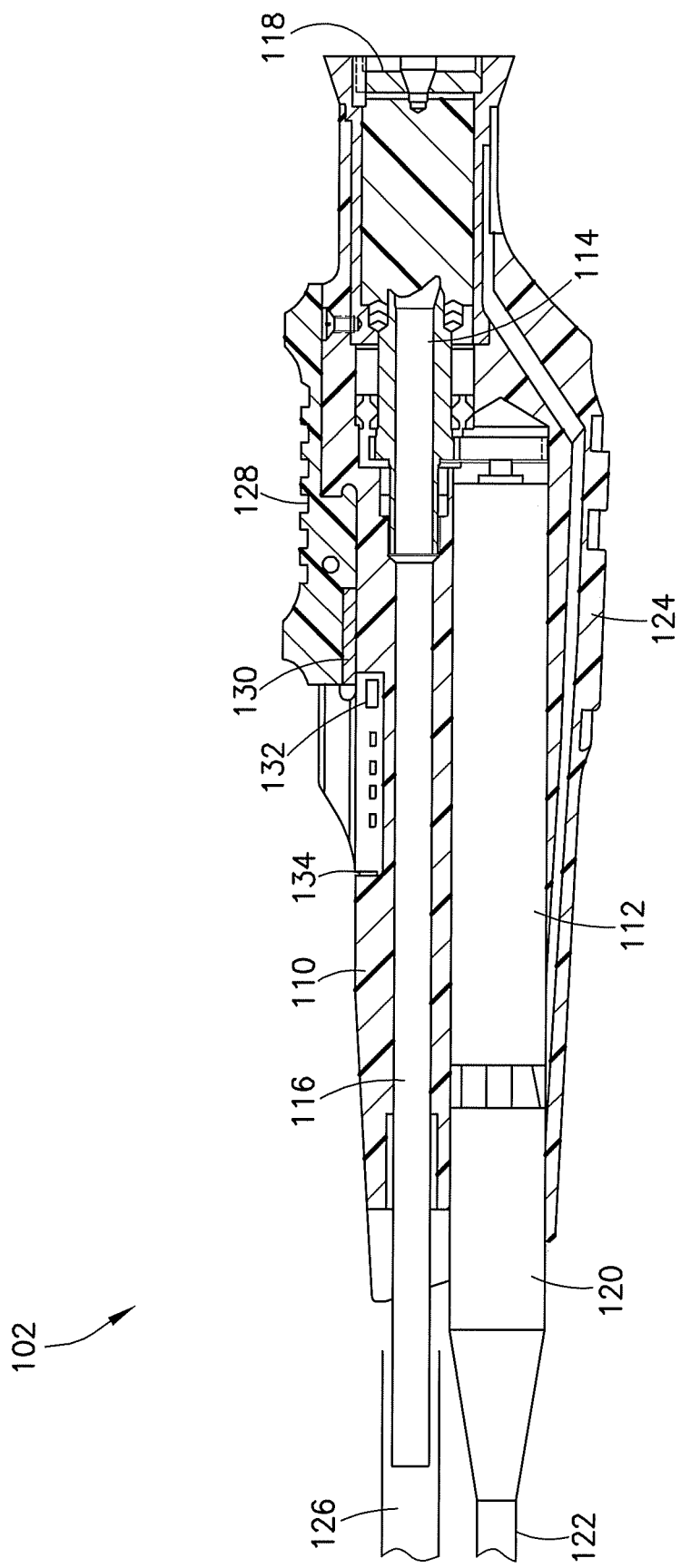
FIG. 3 is a section view of a shaver handpiece of the fluid management system shown in FIG. 2.

Referring now also to FIG. 3, the shaver handpiece 102 comprises a housing 110 which surrounds a motor 112, a coupling 114, and a suction cannula 116. The handpiece 102 is configured such that an attachment 118 (such as a blade, for example) is removably connected to a front end of the handpiece 102. A motor shaft extending from the motor 112 comprises a pinion gear (driving) which is configured to engage with a driven gear on the coupling 114 to provide rotation to the attachment 118. According to various exemplary embodiments, the attachment 118 itself does not rotate, as the attachment 118 is a stationary component that accepts a disposable blade wherein an inner hub (of the attachment 118) engages with the coupling 114 to rotate or oscillate the inner disposable blade. A back end of the handpiece 102 is configured to receive a cable connector 120 of a cable 122 for connection to the motor 112. Also at the back end is an interface portion between the suction cannula 116 and the shaver tubeset 106. Additionally, activation buttons 124 are provided at the housing 110.

The fluid management system 100 provides for a slider electro-mechanical valve which includes a slider (or fluid control mechanism) 128 with a long magnet 130 which is captured inside and along a bottom portion of the slider 128. The slider 128 (and the magnet 130 along with the slider 128) is configured to move such that the magnet 130 slides above a hall effect sensor 132 which controls the (occluder) valve 105 to restrict the flow through the flexible suction tubeset 106.

Still referring to FIG. 3, the shaver handpiece with the slider suction controller valve is provided with a printed circuit board (PCB) and electronic circuitry configured such that the Hall Effect sensor 132 detects the slider magnet 130 location. Based on the slider location (magnet location), the occluder valve (or fluid occluding member) 105 with an actuator 136 restricts the suction flow proportionally through the shaver tubeset 106 (see also FIG. 4).

Figure 4:
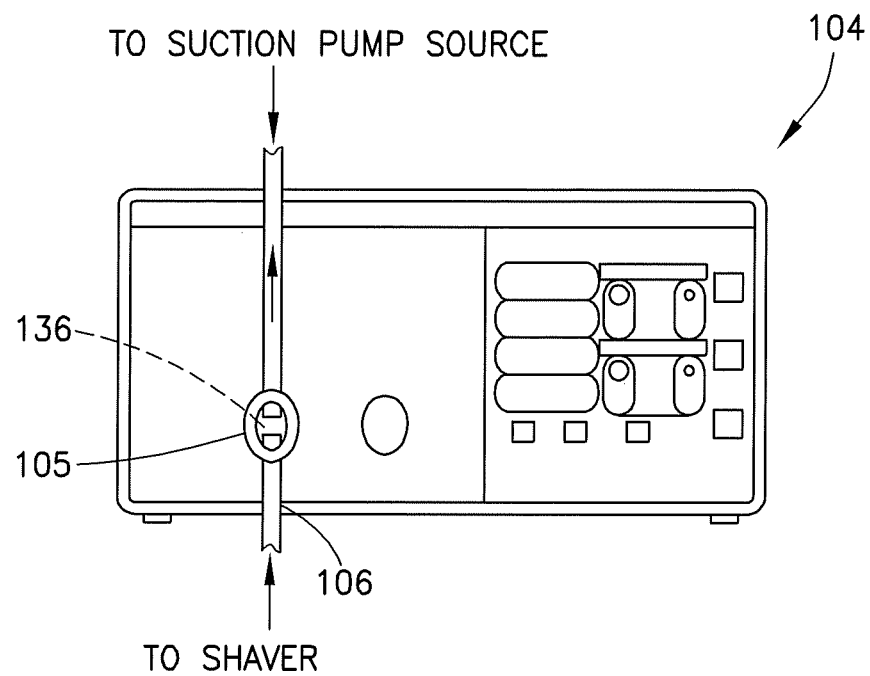
FIG. 4 is a perspective view of a portion of the fluid management system shown in FIG. 2.
Figure 5:
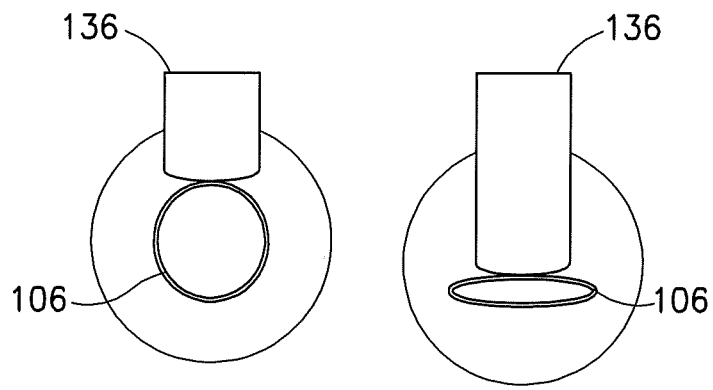
FIG. 5 is an enlarged view of a tube and a valve portion of the fluid management system shown in FIG. 2.

For example, as shown in FIG. 4 the occluder valve 105 is disposed within the shaver console 104 where the shaver tubeset 106 passes through the valve 105. The actuator 136 moves 'in' and 'out' to restrict the flow through the shaver tubeset 106. For example, as shown in FIG. 5 (which illustrates a top section view of the shaver tubeset passing though the occluder valve) the valve actuator 136 is configured to squeeze the tube 106 to restrict the flow (where unrestricted flow is shown in the left hand side of FIG. 5 and restricted flow is shown in the right hand side of FIG. 5).

Figure 6:
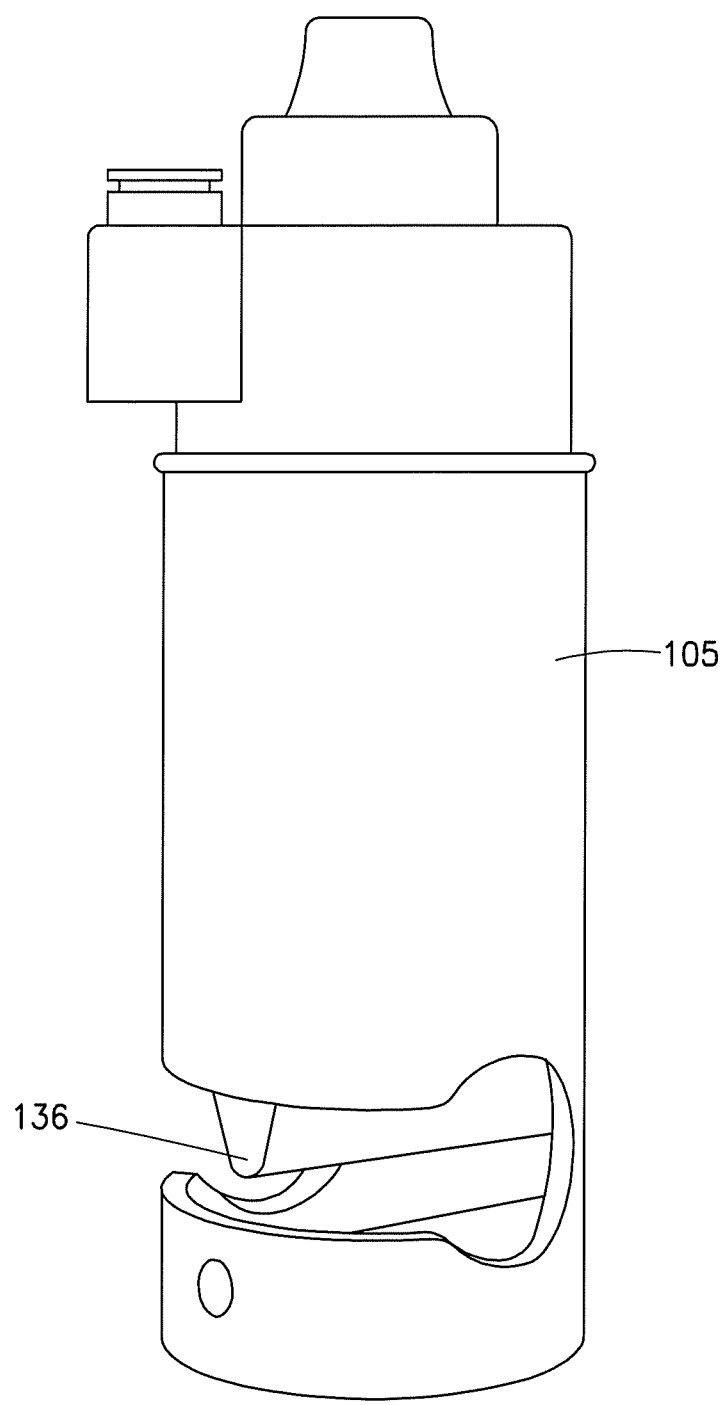
FIG. 6 is perspective view of a valve of the fluid management system shown in FIG. 2.

The valve 105 may be a pinch valve manufactured by Resolution Air, for example (see FIG. 6). However in alternate embodiments, any suitable valve may be provided. In the example described above, the pinch valve 105 and the actuator 136 are controlled by a stepper motor of the console 104.

Figure 7:
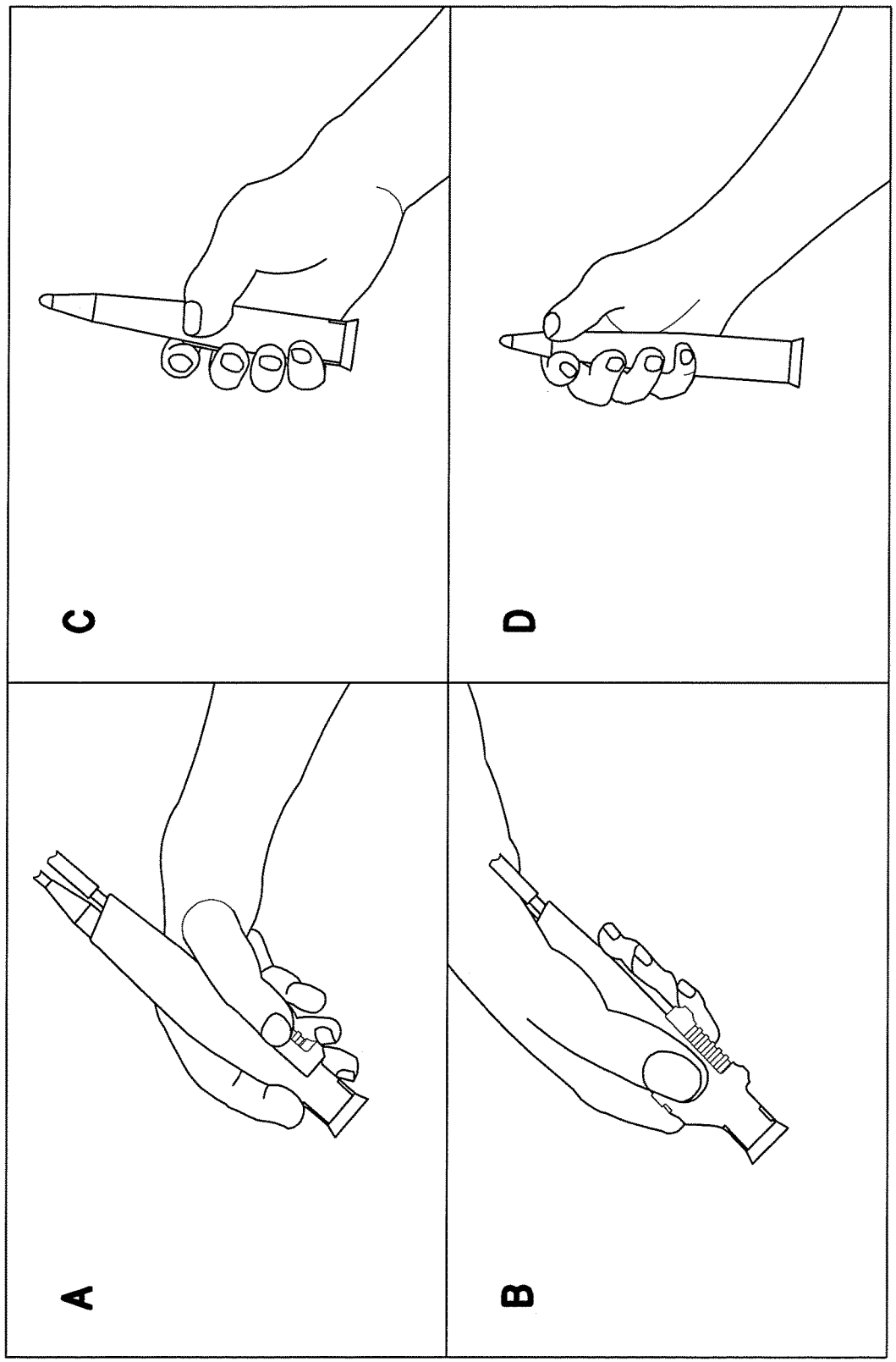
FIG. 7 provides various perspective views of different hand grip positions of the shaver handpiece of the fluid management system shown in FIG. 2.

According to various exemplary embodiments of the invention, the slider electromechanical suction control can be placed away from the suction cannula pathway. This feature enables the user to have different hand grip positions. For example, as shown in FIG. 7 a variety of ergonomic handgrips such as a pen holding grip (see "A"), a grabbing grip (see "B"), a clasping downwards grip (see "C"), and a clasping grip (see "D"). Through research, the slider valve has the most comfortable handling and easily reachable configuration through the different types of ergonomic grips.

Figure 1:
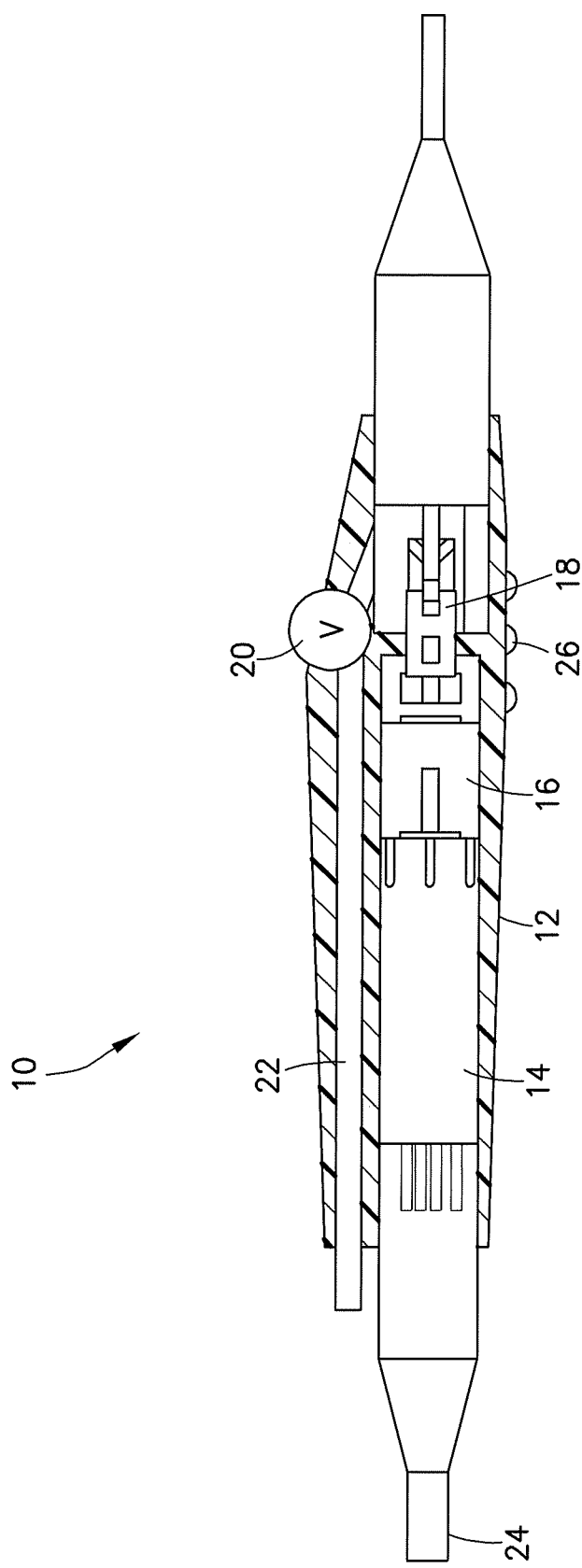
FIG. 1 is a section view of a conventional medical orthopedic shaver.

Technical effects of any one or more of the exemplary embodiments provide significant advantages over conventional configurations. For example, one advantage of the slider electro-mechanical valve is that it has no direct contact to the fluid passing through the suction cannula. Therefore, the cleaning and sanitizing of the suction cannula is much simpler and easily achieved. A tube brush can be used to clean straight through the suction cannula in much more effective and efficient way. The straight through design also enables a more efficient flow due to less turbulence and provide a better laminar flow. The straight through design also minimizes the chance of clogging during a procedure whereas conventional configuration a prone to this issue. Whereas in the conventional configurations, the suction control valve has limitations due to its location in the handpiece. For example, it is usually placed within the suction cannula of the handpiece shaver. In addition, the cleaning and sanitizing of the conventional handpieces is not simple and it could be a major factor for reuse the handpiece shaver. This is due to the difficulty of accessing certain places with a cleaning brush due to the inherent design of having a through hole on a cylindrical barrel and the angled suction path (for example see FIG. 1). Furthermore, the valve assembly with the conventional handpiece shaver requires a precise carefulness assembly to insure proper seal within the suction pathway.

Additional technical effects of any one or more of the exemplary embodiments provide for a fluid suction line that is remotely controlled by a magnetic sensor through a slider mechanism. Another technical effect of any one or more of the exemplary embodiments provide for a magnetic sensor to remotely control the fluid flow. Another technical effect of any one or more of the exemplary embodiments provide for ways to ergonomically handle the shaver handpiece shaver with easy access to the suction control slider valve.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a fluid management assembly is disclosed. The fluid management assembly comprises: a handpiece; a slider based fluid control mechanism housed in the handpiece; and a fluid occluding member configured to be in communication with the fluid control mechanism; the fluid occluding member being separate from the handpiece.

A fluid management assembly as above, wherein the slider based fluid control mechanism comprises a magnet based sensor.

A fluid management assembly as above, wherein the fluid occluding member is disposed inside an equipment console separate from the handpiece.

A fluid management assembly as above, wherein the equipment console comprises an actuator.

A fluid management assembly as above, wherein the actuator is configured to squeeze a tube of the assembly to restrict flow.

A fluid management assembly as above, wherein the fluid occluding member comprises a valve.

A fluid management assembly as above, wherein fluid occluding member is configured to have no direct contact with fluid passing through a suction cannula of the assembly.

A fluid management assembly as above, wherein the handpiece further comprises a suction cannula and a drive shaft, and wherein an entire length of the suction cannula is substantially concentric with the drive shaft.

A fluid management assembly as above, wherein the handpiece further comprises a motor and a printed circuit board, wherein the suction cannula is between the motor and the printed circuit board.

In another exemplary embodiment, a method is disclosed. The method comprises: providing a handpiece; connecting a slider based fluid control mechanism to the handpiece; and providing a fluid occluding member configured to be in communication with the fluid control mechanism, wherein the fluid occluding member is separate from the handpiece.

The method as above, wherein the slider based fluid control mechanism comprises a magnet based sensor.

The method as above, wherein the fluid occluding member is disposed inside an equipment console separate from the handpiece.

The method as above, wherein the equipment console comprises an actuator.

The method as above, wherein the actuator is configured to squeeze a tube of the assembly to restrict flow.

The method as above, wherein the fluid occluding member comprises a valve.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A handheld medical device comprising:
   a housing forming a handpiece;
   a motor in the housing, the motor including a driveshaft;
   a coupling;
   at least one gear connecting the coupling to the driveshaft;
   a control on the housing, the control including a printed circuit board; and
   a suction cannula in the housing, wherein the suction cannula is located at least partially between the motor and the printed circuit board.

2. The handheld medical device of claim 1, where the coupling is configured to have an attachment connected thereto, where the coupling is configured to be between the attachment and the suction cannula when the attachment is attached to the handpiece.

3. The handheld medical device of claim 1, where the control comprises a slider slidably located on the housing of the handpiece, a magnet and a magnet based sensor.

4. The handheld medical device of claim 3, where the magnet is on the slider, and where the magnet is configured to longitudinally slide with the slider in a linear path on the housing.

5. The handheld medical device of claim 3, where the printed circuit board is configured to be electrically connected to an equipment console separate from the handpiece, where the equipment console comprises a fluid occluding device configured to be in communication with the printed circuit board such that the control on the housing is configured to at least partially control the fluid occluding device of the equipment console.

6. An apparatus comprising:
   the handheld medical device of claim 5; and
   the equipment console having the handheld medical device connected thereto.

7. The apparatus as in claim 6, where the fluid occluding device comprises an actuator, where the actuator is configured to squeeze a suction tube to restrict flow, and where movement of the actuator is controlled, at least partially, by the printed circuit board on the housing.

8. The apparatus as in claim 7, where the suction tube extends from the suction cannula to the actuator, and where the fluid occluding device is configured to have no direct contact with fluid passing through the suction cannula or the suction tube.

9. A fluid management assembly comprising:
   a handpiece;
   a slider based fluid control mechanism housed on the handpiece;
   where the handpiece comprises a suction cannula, a coupling, a motor comprising a driveshaft, and at least one gear connecting the coupling to the driveshaft, where the coupling is configured to have an attachment connected thereto, where the coupling is configured to be between the attachment and the suction cannula when the attachment is attached to the coupling; and
   where the slider based fluid control mechanism is configured to be connected to a fluid occluding device, with the fluid occluding device being separate from the handpiece.

10. The assembly of claim 9, where the slider based fluid control mechanism comprises a magnet based sensor.

11. The assembly of claim 9, where an entire length of the suction cannula is substantially concentric with the coupling.

12. The assembly of claim 9, where the handpiece further comprises a printed circuit board, and where the suction cannula is at least partially located between the motor and the printed circuit board.

13. The assembly of claim 9, where the handpiece further comprises a magnet based sensor, and where the suction cannula is at least partially located between the motor and the magnet based sensor.

14. A fluid management assembly comprising:
   a handpiece; and
   a fluid control mechanism housed on the handpiece and configured to be connected to a fluid occluding device;
   wherein the handpiece comprises a suction cannula, a coupling, a motor comprising a driveshaft, and at least one gear connecting the coupling to the driveshaft;
   wherein the coupling is configured to have an attachment connected thereto; and
   wherein the coupling is configured to be between the attachment and the suction cannula when the attachment is attached to the coupling.

15. The assembly of claim 14, wherein the fluid control mechanism comprises a slider slidably located on the handpiece.

16. The assembly of claim 15, wherein the fluid control mechanism further comprises a magnet and a magnet based sensor.

17. The assembly of claim 16, wherein the magnet is located on the slider, and wherein the magnet is configured to longitudinally slide with the slider in a linear path on the handpiece.

* * * * *